United States Patent [19]

Jönsson et al.

[11] Patent Number: 5,182,099
[45] Date of Patent: Jan. 26, 1993

[54] PREPARATION FOR PREVENTION OF EMISSION OF MERCURY FROM AMALGAM FILLINGS AND METHOD

[75] Inventors: Eston Jönsson; Roland Waern, both of Värnamo, Sweden

[73] Assignee: Swedima, Inc., Rockford, Ill.

[21] Appl. No.: 750,474

[22] Filed: Aug. 27, 1991

Related U.S. Application Data

[63] Continuation-in-part of Ser. No. 752,458, Aug. 27, 1991, abandoned.

[51] Int. Cl.$^5$ .......................... A61K 7/16; A61K 9/68; A61K 31/095
[52] U.S. Cl. ........................ 424/49; 424/703; 424/705; 424/48; 424/440; 424/2; 424/10; 106/35; 433/226; 433/228.1; 433/229; 433/215
[58] Field of Search ..................... 424/49–53, 424/703–705, 49, 903, 705, 2, 10, 48, 40; 106/35; 433/215, 226, 228.1, 229

[56] References Cited

U.S. PATENT DOCUMENTS

| | | | |
|---|---|---|---|
| 1,379,046 | 5/1921 | Rogers | 424/53 |
| 1,379,744 | 5/1921 | Congreve | 424/49 |
| 1,558,160 | 10/1925 | Gearhart | 424/58 |
| 5,100,653 | 3/1992 | Campo | 424/49 |

FOREIGN PATENT DOCUMENTS

| | | |
|---|---|---|
| 242553 | 10/1987 | European Pat. Off. . |
| 326884 | 8/1989 | European Pat. Off. . |
| 9010433 | 9/1990 | PCT Int'l Appl. . |
| 8900872A | 9/1990 | Sweden . |
| 463189B | 10/1990 | Sweden . |

OTHER PUBLICATIONS

Campo C.A. 112:124959v (1990) 7 EP 326884, Aug. 8, 1989.
Campo C.A. 108:624992 (1988) 7 EP 242553, Oct. 28, 1987.

*Primary Examiner*—Shep K. Rose
*Attorney, Agent, or Firm*—Robert F. Green

[57] ABSTRACT

A method of preventing or decreasing the emission of mercury vapor in the mouth, from a mercury amalgam filling, comprising contacting the amalgam filling with an oral composition containing sulfur in an amount sufficient to reduce or eliminate the emission of mercury or mercury vapor. The oral composition may be in the form of a toothpaste, chewing gum, mouthwash water, mouth spray, or the like.

2 Claims, 2 Drawing Sheets

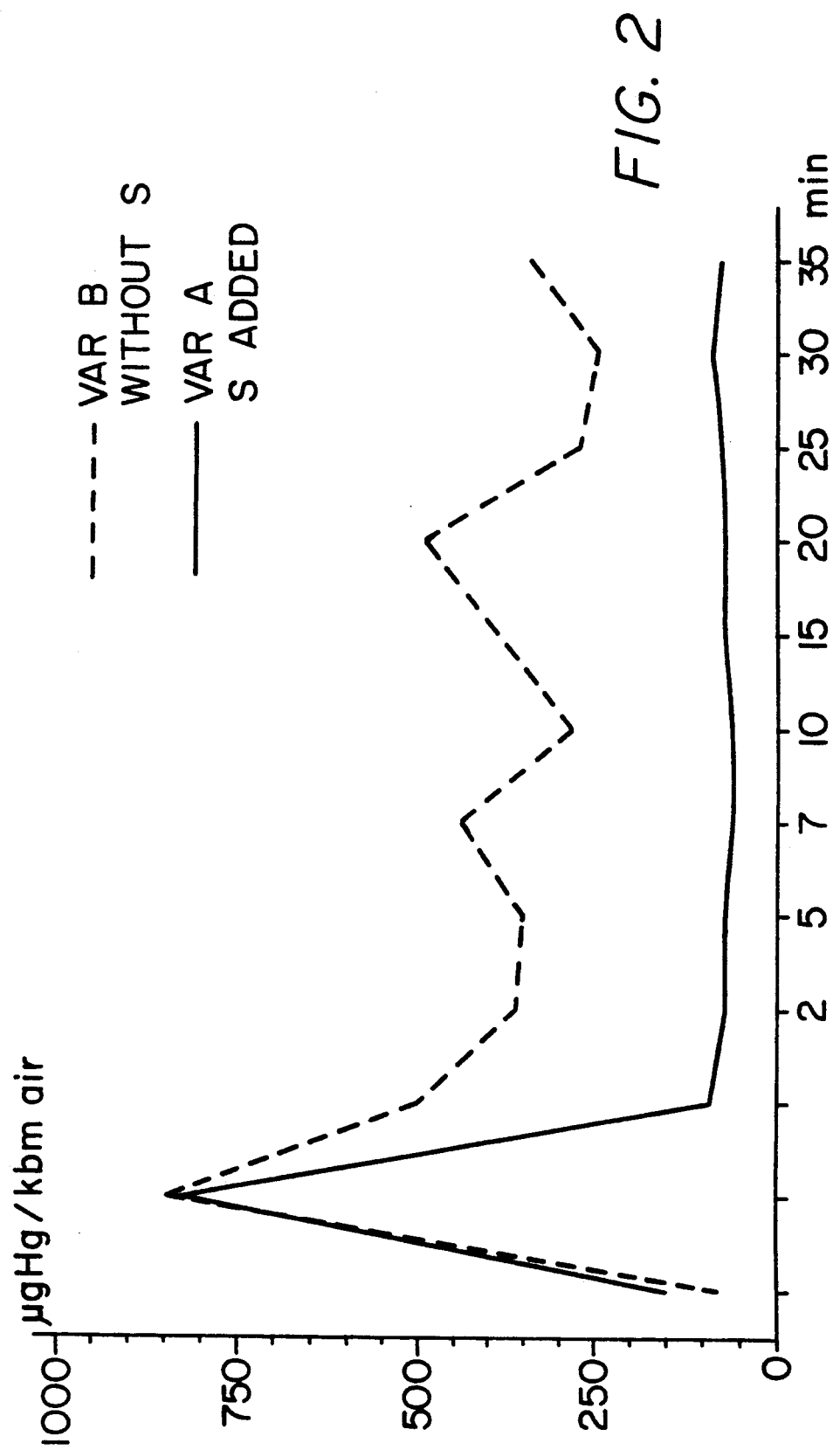

PREPARATION FOR PREVENTION OF EMISSION OF MERCURY FROM AMALGAM FILLINGS AND METHOD

CROSS REFERENCE TO RELATED APPLICATION

This application is a continuation-in-part of U.S. application Ser. No. 752,458, filed on Aug. 27, 1991, now abandoned, which in turn was a National Phase application based upon PCT application No. 90/00157, filed Dec. 3, 1990, in turn based upon Swedish patent application No. 8900872-6, filed Mar. 13, 1989, priority for which is claimed.

This invention relates to preparations that are intended for use in the human oral cavity to prevent and/or decrease the amount of mercury and/or mercury vapor that is emitted from mercury-containing amalgam fillings in teeth.

The invention also includes a method of preventing the emission of mercury and mercury vapor from amalgam fillings in teeth.

BACKGROUND OF THE INVENTION

For many years amalgam has been used extensively in the restoration of human teeth. The amalgam is an alloy of mercury and other metals such as silver, tin, copper and zinc. The amount of mercury in these types of amalgam is mainly from about 50 to about 70%, by weight.

Recent studies have demonstrated that metallic mercury is released from the amalgam as a vapor in the human mouth. This emission of mercury vapor is a continuing, ongoing process, but the amount released per second demonstrates significant fluctuations, depending upon several factors, such as the temperature of the amalgam filling, and whether the filling is exposed to abrasion, such as chewing, brushing, grinding or other types of mechanical force. Accordingly, several studies have shown that the emission of mercury vapor increases significantly during periods of chewing or the like, when compared to periods of no mechanical stress.

In the publication "Striden om amalgamet", page 21 Källa 33, by the Swedish Federal Research Department report from 1989, measurements are reported of this emission of mercury vapor. Apparently, these measurements are made on the total exhaled air from test persons and are, accordingly, demonstrating "diluted" sum numbers from all the teeth in each person's mouth. Reported results are shown in FIG. 1. In this Figure, curve I shows a series of measurements made on eleven test persons without amalgam fillings. Curve II shows a series of measurements made on nine test persons, wherein each person has up to four amalgam fillings on the occlusal surfaces. Curve III shows a series of measurements made on ten test persons, wherein each person has more than ten amalgam fillings on their occlusal surfaces. The curves show how the emission of mercury vapor measured in micrograms per cubic meter of the exhaled air varies in time when the test persons are chewing.

Curve I of FIG. 1 also shows that test persons with no amalgam filling in their teeth still emit a small amount of mercury vapor, and this amount is not influenced by chewing. Such emission is probably due to the presence of mercury deposited in the human body through means other than amalgam fillings, and is continuously emitted.

From curve II of FIG. 1, it can be seen that the amount of mercury vapor in the exhalation air increases sharply and very quickly when chewing is started. Further, even after chewing has ceased for 30 minutes, the amount of mercury vapor only slowly decreases toward the starting value.

Curve III of FIG. 1 demonstrates a very sharp increase in the emission of mercury vapor. The maximum values after 30 minutes of chewing are many times higher than the starting point before the chewing was initiated. Further, the increased values remain during a long time after completed chewing. Since the emitted mercury vapor probably, at least partly, is absorbed by the human body, a potentially significant health risk is presented.

A need therefore exists for a method by which the amount of mercury and mercury vapor emitted from dental amalgam may be eliminated or reduced so that the amount of mercury being exposed to the human body can be made significantly reduced. Further, a need exists for a composition that is capable of significantly reducing the emission of mercury vapor from mercury-containing amalgam fillings.

BRIEF DESCRIPTION OF THE DRAWINGS

FIG. 2 is a plot showing the amount of mercury released over a period of time, during and subsequent to brushing, using toothpaste with and without sulfur.

SUMMARY OF THE INVENTION

Figure 1:
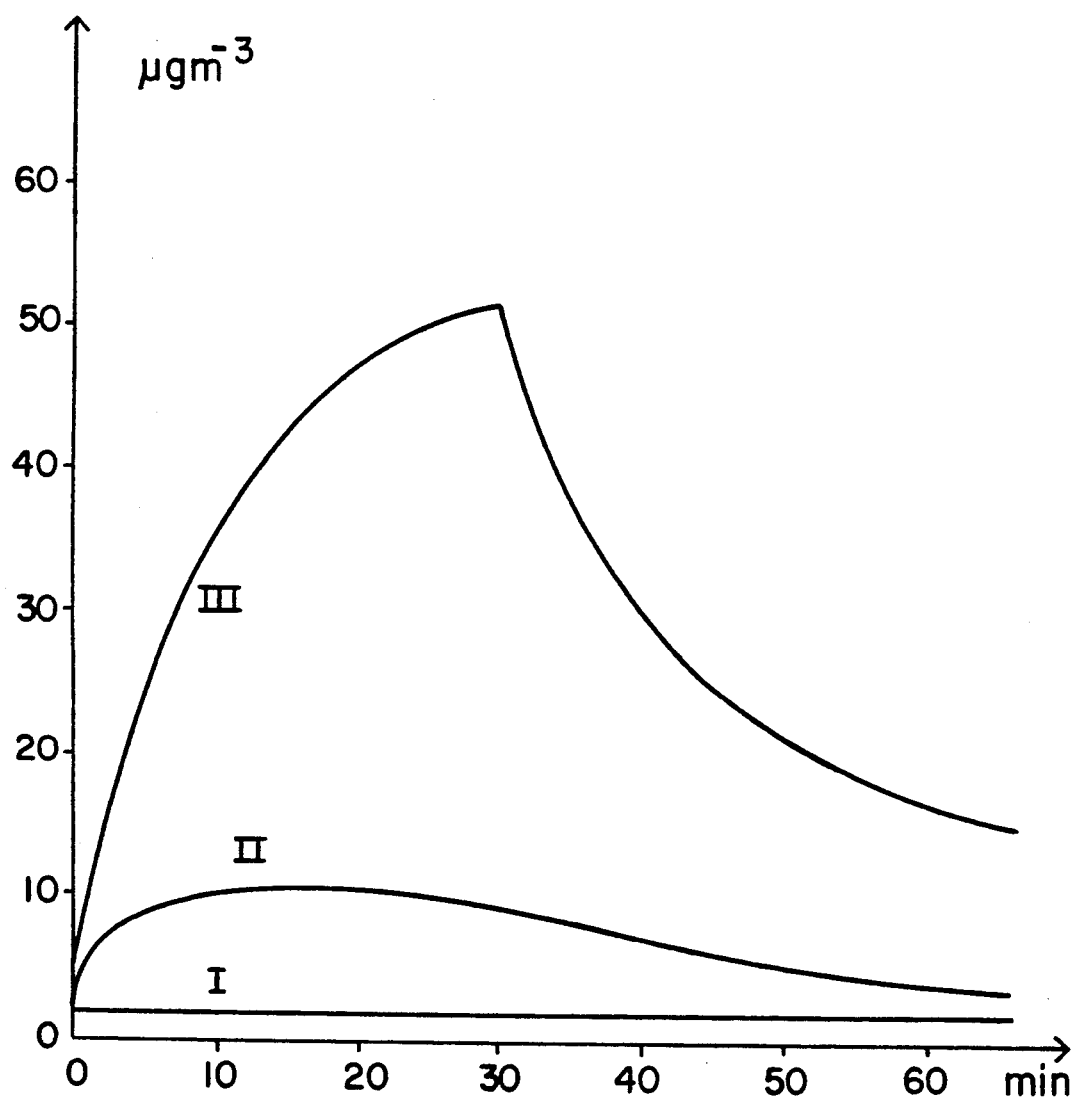
FIG. 1 contains three curves showing the emission of mercury vapor over a period of time, Curve I representing a person with no mercury amalgam filling, Curve II showing the effect of chewing upon the release of mercury vapor in persons having up to four amalgam fillings, and Curve III showing the effect of chewing on persons having more than ten amalgam fillings.

Surprisingly, there has now been found a method for reducing or eliminating mercury emission from dental amalgam which comprises contacting the dental amalgam, as by brushing, rinsing or masticating, with a composition comprising sulfur. Oral compositions, such as toothpastes, tooth powders, mouth washes, chewing gums, mouth sprays, lozenges, sachets, dental cooling fluids, and the like, comprising sulfur and a pharmaceutically-acceptable carrier, are also provided, which, when placed in contact with mercury-containing dental amalgam, cause a reduction or elimination of mercury vapor emission from such amalgams.

DETAILED DESCRIPTION OF THE PREFERRED EMBODIMENTS

The invention in its most general form concerns the use of sulfur to prevent or reduce the emission of mercury or mercury vapor from amalgam fillings in teeth. In connection with this, the invention also includes the use of sulfur in preparations for this purpose.

In one embodiment, the product of the present invention also contains, besides sulfur, a grinding or polishing substance.

In a second embodiment the product is characterized in that it is a toothpaste. Such a toothpaste may contain, in addition to the sulfur, one or more of the following ingredients:

Aluminum hydroxide
Blue #1
Calcium carbonate

Carbomer 956
Carboxymethyl cellulose
Carrageenan
Cellulose gum
Dicalcium phosphate
Dicalcium phosphate dihydrate
Disodium phosphate
Disodium pyrophosphate
Eggshell powder
FD & C Blue #1
Flavor
Glycerin
Hydrated silica
Hydroxy ethyl cellulose
Methyl paraben
Mica
Myrrh
p-Hydroxy benzoic acid
Pareth 15-7 and 15-9
PEG-6
PEG-8
PEG-12
PEG-32
Peppermint oil
Polymethylmethacrylate
Potassium nitrate
Propolis
Propyl paraben
Propylene glycol
Red #30 Lake
Red #33
Red #40
SD Alcohol 38B
Silica
Silicic acid
Sodium benzoate
Sodium bicarbonate
Sodium carrageenan
Sodium chloride
Sodium fluoride
Sodium lauryl sarcosinate
Sodium lauryl sulfate
Sodium metaphosfate
Sodium monofluoro phosphate
Sodium phosphate
Sodium saccharin
Sorbitol
Spearmint oil
Tetra-potassium pyrophosphate
Tetra-sodium pyrophosphate
Titanium dioxide
Trisodium phosphate
Water
Water hydrated silica
Xanthan gum
Xylitol
Yellow #10
Zinc citrate trihydrate
Zirconium silicate In a third embodiment of the invention the product is characterized in that it is a chewing gum. Such a chewing gum may contain, in addition to the sulfur, one or more of the following ingredients:
Acesulfane potassium
Artificial color
BHT
Caramel color
Corn syrup
Dextrose
FD & C Yellow #6
Glycerin
Mannitol
Natural and artificial flavor
Gum base
Sodium saccharin
Softeners
Sorbitol
Sugar In a further embodiment of the invention, the product is in a liquid state in the form of a mouth wash water or mouth spray. Such a mouth wash Water or mouth spray may contain, in addition to the sulfur, one or more of the following ingredients:
Acetic acid
Allantoin
Benzoic acid
Citric acid
Domiphen bromide
Ethylpyridinium Chloride
Glycerin
FD & C #40, Blue #1, Yellow #5 and #10 and Green #3
Flavor
Poloxamer 407
Polysorbate 20
PVM/MA copolymer
Red 33
SD Alcohol
Sodium acetate
Sodium Benzoate
Sodium bicarbonate
Sodium borate
Sodium chloride
Sodium citrate
Sodium fluoride
Sodium lauryl sulfate
Sodium saccharin
Sodium salicylate
Sorbitol
Tetrapotassium phrophosphate
Tetrasodium pyrophosphate
Water
Xanthan gum
Zinc chloride In a further embodiment the product is characterized in that it is a cooling liquid used for dental tools for drilling, grinding, polishing or scaling. Such a cooling liquid may contain water, in addition to the sulfur.

In a further embodiment, the product is characterized in that it contains, in addition to the sulfur, a drying, coagulating, or curing adhesive, in a pharmaceutically acceptable carrier.

Preferably, the sulfur used in the present invention is in free form, that is as elemental sulfur, when it contacts the amalgam. The sulfur may be initially present as free sulfur, or may be present as a complex or component of a molecular structure, provided that, upon application to the oral cavity, the sulfur is capable of reacting with the mercury to form an insoluble compound or complex. A safe and effective amount is present in the compositions of the present invention.

As a result of practical series of test it has been determined that sulfur, in chemically free form, has the property of preventing or reducing the emission of mercury vapor from amalgam fillings, when added to the oral cavity and especially to amalgam fillings. The exact chemical or physical processes making this possible, are still unknown, but probably the sulfur, together with emitted mercury vapor, forms mercury sulfide, which is extremely difficult to dissolve in either water or acidic solutions. Consequently, the mercury sulfide, if swallowed, should pass through the human body in a chemically unmodified form. Accordingly, sulfur in any form that is capable of reacting with mercury to form mercury sulfide is operable within the scope of the present invention.

As noted, the oral compositions of the present invention comprise a safe and effective amount of sulfur in combination with a pharmaceutically-acceptable carrier. The term "pharmaceutically-acceptable carrier", as used herein, means any suitable vehicle which is non-toxic, which is not reactive with the sulfur, and which can be used to deliver or apply the present compositions to the oral cavity. Such carriers include the usual components of mouthwashes, toothpastes, tooth powders, prophylaxis pastes, lozenges, chewing gums, mouth sprays, sachets, and the like and are more fully described hereinafter. Dentifrices (including toothpastes, gels and toothpowders) and mouthwashes are the preferred systems.

In general, the pharmaceutically-acceptable carrier can comprise from about 0.1% to about 99.9% by weight of the oral compositions herein, preferably from about 50% to about 99.9%, with from about 80% to about 99% being most preferred. Depending on the type of oral composition desired, the safe and effective amount of sulfur can comprise from about 0.005% to about 50%, usually from about 0.005% to about 5.0%, typically from about 0.01% to about 5%, by weight of the compositions, and preferably from about 0.01% to about 1%, with from about 0.05% to about 0.1% being most preferred. Particular kinds of such compositions are illustrated hereinafter. All percentages and ratios are by weight, unless specified otherwise.

Dentifrice compositions (e.g., toothpastes, toothgels, and toothpowders) generally comprise in addition to the sulfur, a pharmaceutically-acceptable carrier which can comprise the usual and conventional components of these dentifrice compositions. For example, the dentifrices of the present invention may include abrasive polishing material, flavoring agents, sweetening agents, coloring agents, emulsifying agents, water-soluble fluorides, thickening agents, humectants, alcohols, and/or water. A safe and effective amount of the sulfur, in dentifrice compositions of the present invention, can range from about 0.01% to about 50%, with from about 0.01% to about 2% being more preferred, and from about 0.05% to about 0.1% most preferred.

The abrasive polishing material contemplated for use in the dentifrice compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasives, generally have an average particle size ranging between about 0.1 to about 30 microns, preferably between about 5 and about 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the trade name "Syloid" by the W. R. Grace & Company, Davison Chemical Division. Preferred precipitated silica materials include those marketed by the J. M. Huber Corporation under the trade name, "Zeodent", particularly the silica carrying the designation "Zeodent 119". These silica abrasives are described in U.S. Pat. No. 4,340,583, Jul. 29, 1982, incorporated herein by reference.

The abrasive in the dentifrice compositions described herein is generally present at a level of from about 6% to about 70%, preferably from about 15% to about 25%, when the dentifrice is a toothpaste. Higher levels, as high as 90%, may be used if the composition is a toothpowder.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4,051,234, Sep. 27, 1977, incorporated herein by reference.

It is common to have a water-soluble fluoride compound present in dentifrices in an amount sufficient to give a fluoride concentration of from about 0.0025% to about 5.0% by weight, preferably from about 0.005% to about 2.0% by weight, to provide additional anticaries effectiveness. Preferred fluorides are sodium fluoride, stannous fluoride, indium fluoride, and sodium monofluorophosphate. Norris et al., U.S. Pat. No. 2,946,735, issued Jul. 26, 1960 and Widder et al., U.S. Pat. No. 3,678,154, issued Jul. 18, 1972 disclose such salts as well as others.

Water is also usually present in the toothpastes of this invention. Water employed in the preparation of commercially suitable toothpastes should preferably be deionized and free of organic impurities. Water generally comprises from about 10% to about 50%, preferably from about 20% to about 40%, by weight of the toothpaste compositions herein. These amounts of water include the free water which is added plus that which is introduced with other materials, such as with humectants, e.g., sorbitol.

In preparing toothpastes, it is generally necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums, such as gum karaya, gum arabic, and gum tragacanth, can also be used. Colloidal magnesium aluminum silicate or finely divided silica can be used as part of the thickening agent to further improve texture. Thickening agents in an amount from about 0.5% to about 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

For a fuller discussion of the formulation of toothpaste compositions reference is made to Harry's Cosmeticology, Seventh Edition, 1982, Edited by J B Wilkinson and R J Moore, pages 609 to 617.

Another preferred embodiment of the present invention is a mouthwash composition. Conventional mouthwash composition components can comprise the pharmaceutically-acceptable carrier for the present invention. Mouthwashes generally comprise a water/ethyl alcohol solution (water:ethyl alcohol ratio from about 20:1 to about 2:1) and preferably other ingredients such as flavor, sweeteners, humectants and sudsing agents such as those mentioned above for dentifrices. The humectants, such as glycerin and sorbitol give a moist feel to the mouth. Generally, on a weight basis, the mouthwashes of the invention comprise: about 5% to about 60% (preferably about 10% to about 25%) ethyl alcohol; about 0% to about 20% (preferably about 5% to about 20%) of a humectant; about 0% to about 2% (preferably about 0.01% to about 0.15%) emulsifying agent; about 0% to about 0.5% (preferably about 0.005% to about 0.06%) sweetening agent such as saccharin; about 0% to about 0.3% (preferably about 0.03% to about 0.3%) flavoring agent; and the balance water. The amount of surfur in mouthwashes, is from about 0.005% to about 20%, typically from about 0.05% to about 0.1%.

Other embodiments of the oral compositions herein include lozenges and chewing gums. Suitable lozenge and chewing gum components are disclosed in U.S. pat. No. 4,083,955, Apr. 11, 1978 to Grabenstetter et al., incorporated herein by reference.

A chewing gum will typically comprises a gum base, a suitable softener such as glycerine, typically present in an amount from about 1 to about 10 percent, by weight; and a small amount of flavor oils such as cinnamon, peppermint and spearmint oil, such as from about 0.1to about 2 percent, by weight. A humectant such as sorbitol and/or mannitol may also be present, in an amount form about 5 to about 30 percent, by weight. Natural sugars, such as sucrose, fructose, glucose, and dextrose also may be used, and/or artificial sweeteners as described hereinabove.

The pH of the present compositions and/or the pH of such compositions in the mouth can be any pH which is safe for the hard and soft tissues of the oral cavity. Such pH values generally range from about 3 to about 10, preferably from about 4 to about 8.

The compositions of the present invention can be made using methods which are common in the oral products field. For example, toothpaste compositions may be prepared by mixing part of the humectant and water together and heating to 66°-71° C. The fluoride source, if present, is then added along with the sweetener, the sulfur, the opacifier and the flavor. To this mixture is added the abrasive which is mixed in well. The thickener is then slurried with the remainder of the humectant and milled prior to being added to the other components.

The present invention further relates to a method for reducing or inhibiting the release of mercury vapor by contacting the oral cavity, especially the teeth or dentures, with a safe and effective amount of a sulfur. The phrase "safe and effective amount", as used herein, means an amount of sulfur, which is sufficient to reduce or inhibit the release of mercury or mercury vapor from amalgam, while being safe to the hard and soft tissues of the oral cavity. Generally, a total amount of at least about 0.01 grams, preferably at least about 0.025 grams, of the sulfur, in the oral cavity is effective. Generally, the amount used is within from about 0.01 grams to about 5 grams, with from about 0.025 grams to about 1.0 grams being preferred, and from about 0.05 grams to about 0.5 grams being most preferred. The preferred method for contacting the oral cavity for the method of treatment of the present invention involves contacting the amalgam with one or more of the compositions described above, as by brushing the teeth or dentures with a toothpaste composition of the present invention.

The following examples further describe and demonstrate preferred embodiments of compositions and methods of use within the scope of the present invention. The examples are given solely for illustration and are not to be construed as limitations of this invention, since many variations of the present invention are possible without departing from the spirit and scope thereof.

EXAMPLE I

The following composition is representative of a dentrifrice composition of the present invention.

| Component | Weight % |
|---|---|
| Sorbitol (70% aqueous solution) | 35.000 |
| Water | 29.351 |
| PEG-6<1> | 1.000 |
| Silica Dental Abrasive<2> | 20.000 |
| Sodium Fluoride | 0.243 |
| Titanium dioxide | 0.500 |
| Sodium saccharin | 0.286 |
| Sodium alkyl sulfate (27.9% aqueous solution) | 4.000 |
| Flavor | 1.040 |
| Carboxyvinyl Polymer<3> | 0.300 |
| Carrageenan<4> | 0.800 |
| Sulfur | 7.480 |
| • | 100.000 | n<1>PEG-6 = Polyethylene glycol having molecular weight of 600.
n<2>Precipitated silica identified as Zeodent 119 offered by J. M. Huber.
n<3>Carbopol offered by B. F. Goodrich Company.
n<4>Iota Carrageenan offered by Hercules Chemical Company.

EXAMPLE II

This composition is another example of a dentifrice of the present invention.

| Component | Weight % |
|---|---|
| Sorbitol (as in Example I) | 35.000 |
| Water | 29.653 |
| Sodium Fluoride | 0.243 |
| PEG-6 (as in Example I) | 1.000 |
| Carrageenan (as in Example I) | 0.800 |
| Sodium saccharin | 0.280 |
| Titanium dioxide | 0.500 |
| Flavor | 1.044 |
| Silica Dental Abrasive (as in Example I) | 20.000 |

| Component | Weight % |
| --- | --- |
| Sodium alkyl sulfate (as in Example I) | 4.000 |
| Sulfur | 7.480 |
| * | 100.000 |

The compositions of Example I and II are effective products for reducing mercury and mercury vapor emission, and are cosmetically acceptable.

In the above compositions the abrasive may be replaced by equivalent amounts of other abrasives such as calcium carbonate, calcium pyrophosphate, tricalcium phosphate, dicalcium orthophosphate dihydrate and hydrated alumina with similar results being obtained. Similarly, other thickeners, such as gum arabic and carboxymethyl cellulose may be used as well as other fluoride sources such as stannous fluoride, potassium fluoride, indium fluoride, zinc fluoride and sodium monofluorophosphate. Silicas are the preferred abrasives when fluoride sources are used in the compositions. Other polyepoxysuccinic acid polymers having mass average molecular weights above about 500 may also be used in equivalent amounts in place of the 1000 molecular weight material. Daily use of 1 gram of the compositions in Examples I or II to brush the user's teeth or dentures results in inhibition and reduction of emission of mercury and mercury vapor from dental amalgam.

EXAMPLE III

The following mouthwash composition is another composition of the present invention.

| Component | Weight % |
| --- | --- |
| SDA 40 Alcohol | 8.00 |
| Flavor | 0.08 |
| Emulsifier | 0.08 |
| Sodium Fluoride | 0.05 |
| Glycerin | 10.00 |
| Sweetener | 0.02 |
| Benzoic acid | 0.05 |
| Sodium hydroxide | 0.20 |
| Dye | 0.04 |
| Water | 76.48 |
| Sulfur | 5.00 |
| * | 100.00 |

EXAMPLE IV

The following is a lozenge composition of the present invention.

| Component | Weight % |
| --- | --- |
| Sorbitol | 17.5 |
| Mannitol | 17.5 |
| Starch | 13.6 |
| Sweetener | 1.2 |
| Flavor | 11.7 |
| Color | 0.1 |
| Sulfur | 4.4 |
| Corn syrup | balance |

EXAMPLE V

The following is a chewing gum composition of the present invention.

| Component | Weight % |
| --- | --- |
| Sorbitol crystals | 38.44 |
| Paloja-T gum base<1> | 20.00 |
| Sorbitol (70% Aqueous solution) | 22.00 |
| Mannitol | 10.00 |
| Glycerin | 7.56 |
| Flavor | 1.00 |
| Sulfur | 1.00 |
| * | 100.00 | n<1>Supplied by L. A. Dreyfus Company

The compositions of Examples III, IV and V are also effective mercury vapor-reducing products and are cosmetically acceptable. Daily use of a composition of Examples III, IV, or V by contacting with the oral cavity of the user results in inhibition and reduction of the emission of mercury and mercury vapor from dental amalgam.

EXAMPLE VI

Through pilot tests, where teeth with amalgam fillings were polished with a rubber cup using a preparation consisting of a mixture of sulfur and vaseline, the inventors have observed that after such a polishing, the emission of mercury vapor is reduced or disappears to a very large extent. The measurements of the emission of mercury vapor have in this connection been carried out by means of a nozzle close to the treated amalgam surface, from which the air has been sucked out and transported via a tube to a photospectrometer. The sulfur contents, that have been used in this connection, are high, preferably 5 weight % or more.

Further series of tests have been carried out to verify the effects of sulfur also in lower concentrations. At these tests first of all a "rest point" has been measured, whereby the emission of mercury vapor has been registrated over an "undisturbed" or untreated tooth by means of a nozzle close to the amalgam surface of the tooth. All the registered values are presented in microgram mercury per cubic meter of air. After measurement of the "rest point" or the initial value the actual tooth has been polished under standardized circumstances with a rubber cup covered with ordinary toothpaste, commercially sold under the name of ACTA and in a following test covered with the same toothpaste but with an added ingredient of chemically free sulfur, where the sulfur content amounts to 1 weight % of the toothpaste.

The results of the series of tests carried out on one test person (subject of experiment) are shown in Table 1. A similar test series on another subject is shown in Table 2. It is worth noting that the subject of experiment 1 is a dentist and therefore, through his profession, supposedly has been exposed to mercury to a great extent. Furthermore, he had a considerable number of amalgam fillings. Consequently, mercury could be found as a "disturbance", emitted partly via the respiratory organs and partly from teeth in the environment. Test person 2 has a comparatively small number of amalgam fillings and has probably not been exposed to mercury to a considerable extent through other sources.

From the measured values shown in Table 1 it can be seen that the amalgam fillings continuously, i.e. at rest, emit a considerable amount of mercury vapor. After polishing with ACTA toothpaste, with no added ingredients, the content of emitted mercury vapor increased drastically, at least by a factor 2, up to a factor of 10–15.

After polishing with ACTA, toothpaste with 1 weight % of sulfur added, the contents of mercury in the sucked (inhaled) air at every tooth decreased considerably. Thereby most of these values are lower than the originally measured "rest point". It should also be mentioned that the polishing with this toothpaste with sulfur added occurred immediately after the measurements were taken showing the increased values after polishing with toothpaste with no ingredient added.

From Table 2 it is obvious that the measured values are at about the same or a somewhat lower level than for person 1. Also, in this case, a considerable increase of the content of mercury vapor was reached in the air that was sucked close to the amalgam surface, after polishing with a toothpaste with no added ingredient. Further, the values confirm, after polishing, with toothpaste with sulfur added, that a considerable reduction of the content of mercury vapor can be obtained.

In addition to the above experiments, it could also be mentioned that mercury vapor from amalgam fillings might be dangerous for the carrier of such fillings as well as for the dental team who is handling or grinding the amalgam fillings. The mercury vapor is consequently an occupational hygienical problem for the dental staff.

Two series of measurement have been carried out on a third subject to demonstrate the lapses of time of the indicated effects. In the first test series, the initial value was determined, whereafter the tooth in question was polished with ACTA toothpaste with no added ingredient. Measurements were made of the content of mercury vapor in the air close to the polished amalgam surface (tooth 46) and thereafter with intervals as per Table 5 and FIG. 2.

The decreasing rate amount of the increased value, if no further measures are taken, very clearly corresponds with the result shown in the above-mentioned publication "Striden om amalgamet". Consequently, after two minutes, the content of mercury vapor has been considerably reduced from the maximum value immediately upon the polishing and has been further reduced by about 50% after half an hour. The conclusion of these experiments is that in spite of a rather quick reduction of the content of mercury vapor immediately upon the treatment or stress, there still remains a very increased value during intervals of one hour or more.

The other experimental series (earlier in time than the one mentioned above) on a third test person, was carried out in order to make clear how long the duration of the reduction of the content of mercury vapor is, after polishing with a sulfur-added toothpaste. Because of the relative position of the test series, the measurements could not be carried out on the same tooth (tooth 46), which was used for the above experiment of duration, but was made on another tooth (tooth 36), explaining why the figures are not directly comparable.

The results of this second series of measurements are also shown in Table 5 and FIG. 2.

The conclusion from these test results are that, the obtained reduction of the content of mercury vapor, if sulfur is added, will remain at about the same level for at least half an hour and probably for a longer time. After aforementioned experiments, two further experimental series have been carried out on person 3, in order to determine the percentage of sulfur that might be optimal in the toothpaste. Here the measurements have been made in such a way that, firstly, an initial value was taken, and then a value after polishing with a toothpaste without added ingredient. Hereafter, the mouth was washed with water, measurements were taken and, after that, polishing was made with a toothpaste with sulfur as an added ingredient, followed by mouth wash and measuring. After that, a renewed polishing was made with a toothpaste free from added ingredient, mouth wash, measuring and polishing with sulfur added toothpaste with a different percentage of sulfur, whereafter mouth wash and measuring were carried out, and so on. In this way the following percentages of admixture were tested: 0.1 weight % of sulfur, 0.05 weight % of sulfur, 0.02 weight % of sulfur, 0.01 weight % of sulfur and 0.005 weight % of sulfur. The measurements have been carried out on two different teeth (the teeth 36 and 46) of the test person 3 and the results are being shown in Table 3.

From the measured values of Table 3 it is possible to make the conclusion that a satisfactory effect is obtained at a percentage of sulfur as low as 0.1 weight %. Further, there remains a good effect also at such a low percentage as 0.01 weight %. Probably an optimal value is therefore somewhere between these limits and it is also probable that enlarged experimental series would confirm that an optimal value is to be found somewhere between 0.05 and 0.1 weight %.

Since it is clear that the favorable influence of the sulfur remains during a rather long time, it might be possible that the figures in Table 3 are impaired by some errors, as the measurements have been carried out in a row. This is illustrated by the fact that the measured values, taken immediately upon polishing with a toothpaste without sulfur ingredient, have a tendency to decrease, the more experiments that have been made. In order to correct this possible cause of error to some extent, it can be speculated that the measured values, after polishing, both with a toothpaste without added ingredient and with toothpaste with sulfur added, have been influenced to the same degree. After converting the test values in this way, so that the measured figures after polishing with a toothpaste without added ingredient are on the same level, the values are as per Table 4.

Also, from the values shown in Table 4, it can be seen that the necessary percentages of sulfur to obtain the desired effect, are very low and can be expected to stay under 0.1 weight %.

The sulfur that has been used in all the pilot tests has been of normal trade quality. When measuring the size of grains in a microscope it has been noted that most of the grains have a size of about 0.025 mm. However, both bigger and smaller particles have been observed, and 0.05–0.001 mm are probable limits of the size of the grains.

The favorable effects of the admixture of sulfur have been confirmed by practical tests with sulfur added to toothpaste of completely conventional type. However, there is no reason to believe that the favorable effect should depend on the way in which the sulfur is supplied. It seems to be clear that the effects are not deteriorated if the sulfur is given in such a way that the sulfur is brought into close contact with the amalgam surfaces. It has also been shown that a favorable effect is obtained with a sulfurous chewing-gum. The invention, however, also is intended to cover a supply through liquid preparations in the form of mouthwash water and mouthspray, which, among other things, can be used in order to decrease the emission of mercury vapor in dental treatment.

It especially is worthy to note that the dental staff in its daily work is exposed to more mercury vapor, to a greater degree, than the average carrier of amalgam fillings. Therefore, the present invention includes dental preparations, used by the dental staff, that have the actual sulfur ingredient added, especially preparations containing grinding or polishing agents.

Further, the invention includes an admixture of sulfur in a preparation base containing a congealing or curing binding agent or adhesive so that the preparation can be brought to the actual tooth surfaces in the form of a congealing, curing or drying varnish which preferably is brought to the amalgam fillings before they are treated. In this case the content of sulfur should be calculated on the dry matter of the actual preparation so that, at the calculation of the content, emitted solvent, if any, is being deducted. Further, the invention includes cooling medium (spray), which is used for cooling dental equipment and instruments, that has an added ingredient of sulfur.

Accordingly, the present invention provides a method for reducing mercury or mercury vapor emission during dental reconstruction or cleaning comprising contacting the amalgam with sulfur before and/or during such reconstruction or cleaning. If drilling is required, the fluid, such as water, used to cool the drill bit during drilling may contain sulfur and in such a fashion the sulfur in the cooling fluid may react with free mercury or mercury vapor that is generated as a result of the drilling. Similarly, the polishing or grinding composition used to clean or repair reconstructed teeth that contain dental amalgam, may also contain sulfur so that during the polishing or grinding, the dental amalgam is contacted with sulfur which may then react with any mercury or mercury vapor that is generated as a result of the polishing or grinding process.

When the preparation according to the invention are in a liquid form, with a low viscosity, the sulfur forms sediments comparatively rapidly with the grain sizes mentioned above (0.05–0.001 mm); thus, such a preparation, already after a short time of storage, must be suspended or mixed once more before it is possible to use it. The invention therefore includes the use of smaller particles in these cases, even particles in the colloidal field, i.e. 0.001–0.000001 mm. Sulfur, in colloidal form, can, of course, also be used in other presented methods, where the increased proportion between the surface of the sulfur and its mass can be expected to raise its activity and thereby strengthen its effect.

As can be seen from the invention as described, it also includes a procedure of reducing or preventing the emission of mercury or mercury vapor from amalgam fillings in teeth. In its most elementary way this procedure concerns the supplying of sulfur to the amalgam filling to bring it into a close contact with the fillings. As to the invention, the sulfur is supplied through a carrier, which has a further purpose, for instance grinding, polishing and reduction of bacterial growth or caries. The sulfur can be mixed in the above-mentioned form and in the above-mentioned percentages. The method also includes bringing the sulfur into a very close contact with the amalgam.

TABLE 1

| Test person I | μg Hg/cu.m. air measured close to the tooth: | | | |
|---|---|---|---|---|
| | 14 | 26 | 36 | 46 |
| Before treatment | 90 | 35 | 80 | 85 |

TABLE 1-continued

| Test person I | μg Hg/cu.m. air measured close to the tooth: | | | |
|---|---|---|---|---|
| | 14 | 26 | 36 | 46 |
| After polishing with Acta toothpaste without added ingredient | 215 | 180 | 850 | 1400 |
| After polishing with Acta toothpaste with 1 weight % sulphur | 50 | 45 | 52 | 95 |

TABLE 2

| Test person II | μg Hg/cu.m. air measured close to the tooth: | | | |
|---|---|---|---|---|
| | 14 | 26 | 36 | 46 |
| Before treatment | 72 | 45 | 90 | 62 |
| After polishing with Acta toothpaste without added ingredient | 510 | 660 | 235 | 220 |
| After polishing with Acta toothpaste with 1 weight % sulphur | 60 | 86 | 120 | 58 |

Polishing with Acta toothpaste without resp. with sulphur added.

TABLE 3

| Start Value μg Hg/cu.m. | Tooth 36 120 | Tooth 46 45 |
|---|---|---|
| Without S | 980 | 1400 |
| 0.1% S | 60 | 135 |
| Without S | 590 | 1100 |
| 0.05% S | 70 | 95 |
| Without S | 880 | 560 |
| 0.02% S | 105 | 150 |
| Without S | 430 | 830 |
| 0.01% S | 110 | 115 |
| Without S | 615 | 850 |
| 0.005% S | 110 | 180 |

TABLE 4

| Start value μg Hg/cu.m. | Tooth 36 120 | Tooth 46 45 |
|---|---|---|
| Without S | 980 | 1400 |
| 0.1% S | 60 | 135 |
| Without S | 980 | 1400 |
| 0.05% S | 116 | 120 |
| Without S | 980 | 1400 |
| 0.02% S | 116 | 375 |
| Without S | 980 | 1400 |
| 0.01% S | 250 | 194 |
| Without S | 980 | 1400 |
| 0.005% S | 174 | 297 |

TABLE 5

Emission of mercury in μg hg/cu.m. of air from two amalgam fillings after polishing with a tooth-paste with an added ingredient of sulphur (tooth 36) and with polishing with a tooth-paste without added ingredient (tooth 46) as a function of time.

| Time (minutes) | Tooth 36 | Tooth 46 |
|---|---|---|
| a | 150 | 75 |
| b | 825 | 845 |
| c | 92 | — |
| 2 | 70 | 360 |
| 5 | 70 | 350 |
| 7 | 60 | 440 |

TABLE 5-continued

Emission of mercury in μg hg/cu.m. of air from two amalgam fillings after polishing with a tooth-paste with an added ingredient of sulphur (tooth 36) and with polishing with a tooth-paste without added ingredient (tooth 46) as a function of time.

| Time (minutes) | Tooth 36 | Tooth 46 |
| --- | --- | --- |
| 10 | 60 | 280 |
| 15 | 70 | 390 |
| 20 | 70 | 490 |
| 25 | 75 | 270 |
| 30 | 86 | 245 |
| 35 | 75 | 240 | a: Initial value.
b: After polishing with a tooth-paste without added ingredient.
c: After polishing with a tooth-paste with 1 weight % of sulphur added.

What is claimed is:

1. A method of preventing or decreasing the emission or mercury vapor in the mouth from a mercury amalgam filling in a tooth in the mouth of a host, comprising contacting the amalgam filling with an oral composition containing sulfur in an amount that is effective for reducing or eliminating the emission of mercury or mercury vapor from the mercury-containing dental amalgam in the mouth of said host.

2. The method of claim 1 wherein the sulfur is present in a toothpaste, a chewing-gum, a mount wash water or a mouth spray which is brought into contact with the amalgam, which composition comprises (a) from about 0.005% to about 1% sulfur; and (b) from about 50% to about 99.9% of a pharmaceutically-acceptable carrier.

* * * * *